US012492363B2

(12) United States Patent
Yang et al.

(10) Patent No.: US 12,492,363 B2
(45) Date of Patent: Dec. 9, 2025

(54) HERRINGBONE-TYPE FLUID GUIDING UNIT AND APPARATUS FOR CONCENTRATING FLUID USING SAME

(71) Applicant: GIST(Gwangju Institute of Science and Technology), Gwangju (KR)

(72) Inventors: Sung Yang, Gwangju (KR); Ji Chul Hyun, Gwangju (KR)

(73) Assignee: GIST(Gwangju Institute of Science and Technology), Gwangju (KR)

( * ) Notice: Subject to any disclaimer, the term of this patent is extended or adjusted under 35 U.S.C. 154(b) by 928 days.

(21) Appl. No.: 16/521,573

(22) Filed: Jul. 24, 2019

(65) Prior Publication Data

US 2019/0382702 A1 Dec. 19, 2019

Related U.S. Application Data

(63) Continuation of application No. PCT/KR2018/000977, filed on Jan. 23, 2018.

(30) Foreign Application Priority Data

Jan. 24, 2017 (KR) ........................ 10-2017-0011273

(51) Int. Cl.
*C12M 3/06* (2006.01)
*B01L 3/00* (2006.01)

(52) U.S. Cl.
CPC ......... *C12M 23/16* (2013.01); *B01L 3/50273* (2013.01); *B01L 3/502761* (2013.01);
(Continued)

(58) Field of Classification Search
CPC ... C12M 23/16; C12M 33/00; C12N 15/1003; B01L 3/50273; B01L 3/502761;
(Continued)

(56) References Cited

U.S. PATENT DOCUMENTS 6,319,719 B1 * 11/2001 Bhullar ............. B01L 3/502746 436/175
2005/0136552 A1 * 6/2005 Buechler .......... G01N 33/54386 436/514

(Continued)

FOREIGN PATENT DOCUMENTS

CN 104525072 A * 4/2015 .......... B01J 19/0093
KR 10-0850235 B 8/2008

(Continued)

OTHER PUBLICATIONS

Wei et al. "Numerical Study of Pillar Shapes in Deterministic Lateral Displacement Microfluidic Arrays for Spherical Particle Separation" IEEE Transactions On Nanobioscience, vol. 14, No. 6, Sep. 2015 (Year: 2015).*

(Continued)

*Primary Examiner* — Dean Kwak
(74) *Attorney, Agent, or Firm* — Studebaker Brackett PLLC

(57) ABSTRACT

The present disclosure relates to a herringbone-type fluid guiding unit and an apparatus for concentrating fluid using same. The herring-bone type fluid guiding unit includes: a front member formed on a flow path and formed so that the width between the left side and the right side widens from a front end part toward the back, with respect to the flow direction of a fluid; and a rear member extending from the front member toward the back, wherein the rear member is provided with a recessed part that is recessed to a specific depth from the rear edge toward the front or with a protruding part that protrudes toward the back.

2 Claims, 11 Drawing Sheets

(52) U.S. Cl.
CPC .................. *B01L 2200/0652* (2013.01); *B01L 2300/0848* (2013.01); *B01L 2300/089* (2013.01)

(58) Field of Classification Search
CPC ..... B01L 2200/0652; B01L 2300/0848; B01L 2300/089; B01L 2300/0816; B01L 2300/0864; B01L 2400/086
See application file for complete search history.

(56) References Cited

U.S. PATENT DOCUMENTS

| | | | | |
|---|---|---|---|---|
| 2011/0294187 | A1* | 12/2011 | Toner | G01N 33/54366 435/177 |
| 2015/0285786 | A1* | 10/2015 | Hahn | B01L 3/502753 435/320.1 |
| 2016/0139012 | A1* | 5/2016 | D'Silva | A61K 35/14 435/6.1 |

FOREIGN PATENT DOCUMENTS

| | | | | |
|---|---|---|---|---|
| KR | 10-1515394 | B | 5/2015 | |
| WO | WO-2011142518 | A1 * | 11/2011 | B01L 3/502761 |

OTHER PUBLICATIONS

International Search Report issued in PCT/KR2018/000977; mailed May 10, 2018.

* cited by examiner

Original
herringbone structure

Reduced-deviation-flow
herringbone structure

HERRINGBONE-TYPE FLUID GUIDING UNIT AND APPARATUS FOR CONCENTRATING FLUID USING SAME

CROSS-REFERENCE TO RELATED APPLICATIONS

This application is a Continuation of International Application No. PCT/KR2018/000977 filed Jan. 23, 2018, which claims benefit of priority to Korean Patent Application No. 10-2017-0011273 filed Jan. 24, 2017, the entire content of which is incorporated herein by reference

TECHNICAL FIELD

The present invention relates to a herringbone-type fluid guiding unit and a fluid concentration apparatus using the same, and more specifically, to a fluid guiding unit formed in a herringbone shape so as to guide cells or fine particles contained in a fluid to one side, and a fluid concentration apparatus using the same.

BACKGROUND ART

Generally, a biological analysis process such as pathogen detection or molecular diagnostics includes a step of separating target cells from a sample, a step of concentrating cells, a step of separating biomolecules, a step of amplifying the biomolecules, a step of performing a hybridization reaction, and a step of detecting.

Among techniques related to the biological analysis process, recently, techniques for extracting proteins or nucleic acids from biological samples such as cells, bacteria, or viruses have been widely used to diagnose, treat, or prevent disease at a genetic level in connection with a nucleic acid amplification reaction technique.

Techniques for extracting proteins or nucleic acids from biological samples are required in various fields such as customized new drug development, forensic medicine, and environmental hormone detection in addition to the diagnosis, treatment, or prevention of diseases.

As a conventional method for extracting proteins or nucleic acids from biological samples, a chemical method using a specific lysis buffer or the like has been mainly used. For example, there has been a method of purifying nucleic acids by treating proteins with sodium dodecyl sulfate (SDS) or proteinase K to solubilize the proteins and then by denaturing and removing the proteins with phenol. However, this consumes a great deal of time since the extraction method using phenol requires many processing steps, and the efficiency of nucleic acid extraction greatly depends on the experience and know-how of researchers, thus resulting in poor reliability.

On the other hand, as another method, a cell lysing microfluidic apparatus for concentrating a sample injected into a channel of a microfluidic chip formed as a herringbone pattern and lysing cells in the sample using a photothermal effect of gold nanoparticles inserted into an inner wall of the channel is disclosed in Korean Patent Registration No. 10-1515394.

However, since an angle at a front end part of the herringbone pattern of the cell lysing microfluidic apparatus is the same as an angle at a rear end part of the herringbone pattern, a pressure drop occurs in a fluid flow at the rear end part of the herringbone pattern when an amount of flow or a flow rate of a fluid is increased so that a coagulation rate of cells contained in the fluid is reduced.

Technical Problem

It is an object of the present invention to provide a herringbone-type fluid guiding unit having an angle at a front end part which is greater than an angle at a rear end part in order to reduce a pressure drop occurring in a fluid flow at the rear end part of a fluid guiding unit having a herringbone pattern, and a fluid concentration apparatus using the same.

Technical Solution

One aspect of the present invention provides a herringbone-type fluid guiding unit, which is provided on a flow path through which a fluid flows and guides cells or fine particles contained in the fluid to one side. The herringbone-type fluid guiding unit includes a front member which is provided on the flow path and formed so that a lateral width thereof increases in a rear direction from a front end part thereof with respect to a flow direction of the fluid, and a rear member extending rearward from the front member and having a recessed part recessed by a predetermined depth forward from a rear edge or having a protruding part protruding in a rear direction.

When the recessed part is formed in the rear member, the recessed part may be formed so that a lateral width thereof decreases in a forward direction from the rear edge of the rear member, an angle between a first imaginary line and a second imaginary line respectively extending from a first apex positioned at a frontmost side toward left and right ends positioned at a rearmost side may be greater than an angle between a third imaginary line and a fourth imaginary line respectively extending from a second apex positioned at a frontmost side of the front member toward left and right ends positioned at a rearmost side of the front member, and the angle between the first imaginary line and the second imaginary line may be 180 degrees or less.

The recessed part may be formed to have an inverted-V shape.

The recessed part may have an angle between the first and second imaginary lines of 160 degrees or more.

When the protruding part is formed in the rear member, the protruding part may extend rearward from the front member and may be formed so that a lateral width thereof decreases in the rear direction.

The protruding part may be formed to have a V shape.

The front member may be formed to have an inverted-V shape.

Another aspect of the present invention provides a fluid concentration apparatus including a main body provided with a flow path through which a fluid containing cells or fine particles to be separated therein flows, a plurality of herringbone-type fluid guiding units which are provided on the flow path so as to interfere with a flow of the fluid to guide the cells or fine particles to be separated toward an inner side surface of the flow path and are arranged to be spaced apart from each other in forward and rearward directions with respect to a flow direction of the fluid, and a discharge part which is provided in the main body at a position spaced apart rearward from the herringbone-type fluid guiding units and collects and discharges the cells or fine particles to be separated which are guided into the inner side surface of the flow path.

The herringbone-type fluid guiding unit may include a front member which is provided on the flow path and formed so that a lateral width thereof increases in a rear direction from a front end part with respect to a flow direction of the fluid, and a rear member extending rearward from the front member and having a recessed part recessed by a predetermined depth forward from a rear edge or having a protruding part protruding in a rear direction.

When the recessed part is formed in the rear member, the recessed part may be formed so that a lateral width thereof decreases in a forward direction from the rear edge of the rear member, an angle between a first imaginary line and a second imaginary line respectively extending from a first apex positioned at a frontmost side toward left and right ends positioned at a rearmost side may be greater than an angle between a third imaginary line and a fourth imaginary line respectively extending from a second apex positioned at a frontmost side of the front member toward left and right ends positioned at a rearmost side of the front member, and the angle between the first imaginary line and the second imaginary line may be 180 degrees or less.

The recessed part may be formed to have an inverted-V shape.

The recessed part may have an angle between the first and second imaginary lines of 160 degrees or more.

When the protruding part is formed in the rear member, the protruding part may extend rearward from the front member and may be formed so that a lateral width thereof decreases in the rear direction.

The rear member may be formed to have a V shape.

The front member may be formed to have an inverted-V shape.

The discharge part may include a first discharge path and a plurality of second discharge paths, which are in communication with the flow path of the main body, and the second discharge paths may be disposed on left and right sides of the discharge part with respect to the first discharge path so that the cells or fine particles to be separated which are guided into the inner side surface of the flow path are introduced to the second discharge paths.

Advantageous Effects

In the herringbone-type fluid guiding unit and the fluid concentration apparatus using the same according to the present invention, the fluid guiding unit for interfering with the fluid is formed to have an angle at a front end part greater than an angle at a rear end part, and thus it is possible to reduce a value of a pressure drop of the fluid flow occurring in in the rear part of the fluid guiding unit so that recovery efficiency of the cells with respect to the fluid can be improved.

SUMMARY

Figure 1:
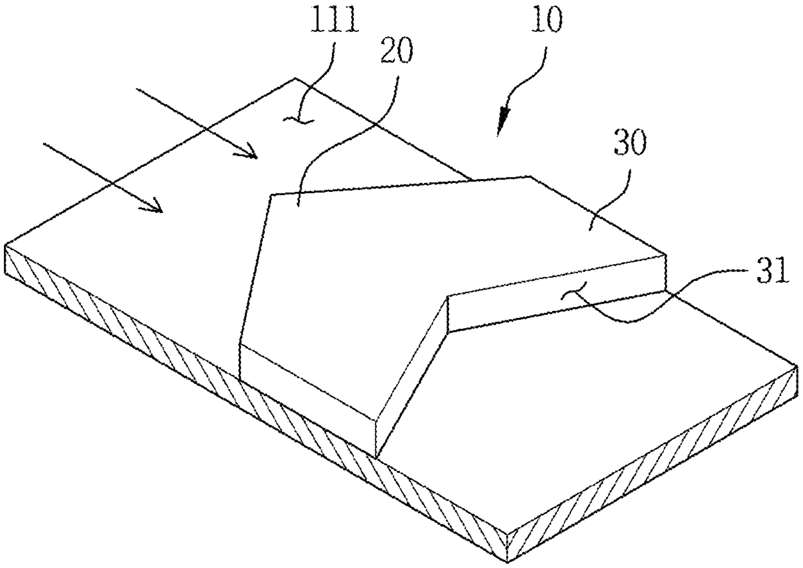
FIG. 1 is a perspective view of a herringbone-type fluid guiding unit according to a first embodiment of the present invention.

A herringbone-type fluid guiding unit of the present invention, which is provided on a flow path through which a fluid flows and guides cells or fine particles contained in the fluid to one side, includes a front member which is provided on the flow path and formed so that a lateral width thereof increases in a rear direction from a front end part thereof with respect to a flow direction of the fluid, and a rear member extending rearward from the front member and having a recessed part recessed by a predetermined depth forward from a rear edge or having a protruding part protruding in a rear direction. When the recessed part is formed in the rear member, the recessed part may be formed so that a lateral width thereof decreases in a forward direction from the rear edge of the rear member, an angle between a first imaginary line and a second imaginary line respectively extending from a first apex positioned at a frontmost side toward left and right ends positioned at a rearmost side may be greater than an angle between a third imaginary line and a fourth imaginary line respectively extending from a second apex positioned at a frontmost side of the front member toward left and right ends positioned at a rearmost side of the front member, and the angle between the first imaginary line and the second imaginary line may be 180 degrees or less.

DETAILED DESCRIPTION

Hereinafter, a herringbone-type fluid guiding unit and a fluid concentration apparatus using the same according to embodiments of the present invention will be described in detail with reference to the accompanying drawings. While the present invention is susceptible to various modifications and alternative forms, specific embodiments thereof are shown by way of example in the drawings and will be described in detail herein. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures. In the accompanying drawings, dimensions of structures are exaggerated to clarify the present invention.

It should be understood that, although the terms "first," "second," and the like may be used herein to describe various elements, the elements are not limited by the terms. The terms are only used to distinguish one element from another element. For example, a first element could be termed a second element, and, similarly, a second element could be termed a first element without departing from the scope of the present invention.

The terminology used herein is for the purpose of describing particular embodiments only and is not intended to be limiting to the invention. As used herein, the singular forms "a," and "an" are intended to include the plural forms as well, unless the context clearly indicates otherwise. It will be further understood that the terms "comprise," "comprising," "include" and/or "including," when used herein, specify the presence of stated features, integers, steps, operations, elements, components, and/or combinations thereof, but do not preclude the presence or addition of one or more other features, integers, steps, operations, elements, components, and/or combinations thereof.

Unless otherwise defined, all terms including technical and scientific terms used herein have the same meaning as commonly understood by one of ordinary skill in the art to which this invention belongs. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

Figure 2:
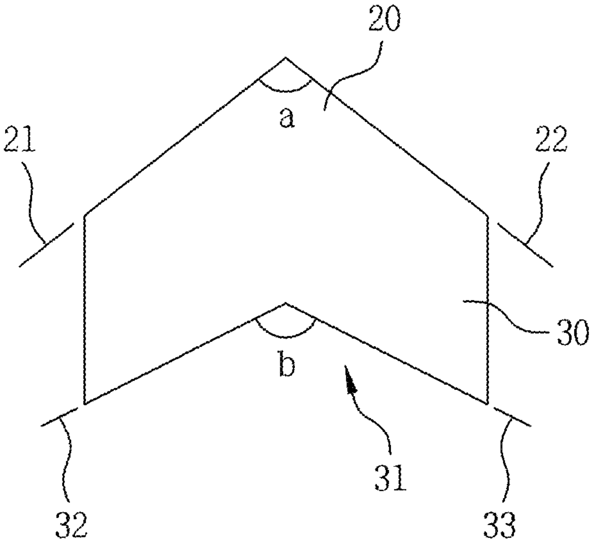
FIG. 2 is a plan view of the herringbone-type fluid guiding unit of FIG. 1.

FIGS. 1 and 2 show a herringbone-type fluid guiding unit 10 according to a first embodiment of the present invention.

Referring to the drawings, the herringbone-type fluid guiding unit 10 includes a front member 20 which is provided on a flow path 111 and formed so that a lateral width thereof increases in a rear direction from a front end part thereof with respect to a flow direction of a fluid, and a rear member 30 extending rearward from the front member 20 and having a recessed part 31 recessed by a predetermined depth forward from a rear edge thereof, as members which are provided on the flow path 111 through which the fluid flows and interferes with the flow of the fluid to guide cells or fine particles contained in the fluid to one side.

The front member 20 is formed to protrude from an inner side surface of the flow path 111 toward a center of the flow path 111. In this case, the front member 20 is formed to have a longitudinal width smaller than a longitudinal width of the flow path 111. Further, the front member 20 may be formed to have an inverted-V shape in which a lateral width increases in the rear direction from a front end part thereof.

The rear member 30 is formed to have a width corresponding to a lateral width of a rear end part of the front member 20 and the recessed part 31 is formed in a rear end part of the rear member 30. The recessed part 31 is formed to have an inverted-V shape in which a lateral width decreases in a forward direction from a rear edge of the rear member 30.

In this case, in the recessed part 31, an angle b between first and second imaginary lines 32 and 33 respectively extending from a first apex positioned at a frontmost side of the rear member 30 toward left and right ends positioned at a rearmost side of the rear member 30 is greater than an angle a between third and fourth imaginary lines 21 and 22 respectively extending from a second apex positioned at a frontmost side of the front member 20 toward left and right ends positioned at a rearmost side of the front member 20, and the angle b between the first and second imaginary lines 32 and 33 may be 180 degrees or less. Further, in the recessed part 31, the angle b between the first and second imaginary lines 32 and 33 may be 160 degrees or more.

Figure 3:
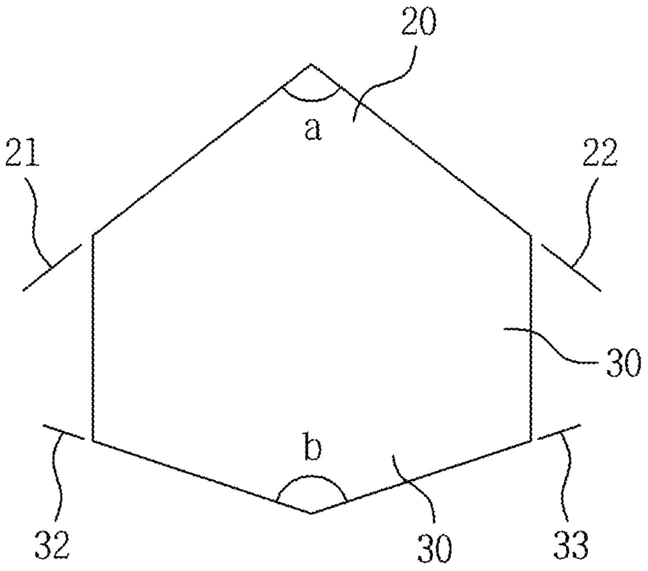
FIG. 3 is a plan view of a herringbone-type fluid guiding unit according to a second embodiment of the present invention.

Meanwhile, FIG. 3 shows a rear member 30 according to a second embodiment of the present invention.

Elements having the same functions as those in the above drawings are denoted by the same reference numerals.

Referring to the drawing, in the rear member 30, a protruding part is formed to extend rearward from the front member 20 and protrude in a rear direction. In this case, the protruding part is formed so that a lateral width thereof decreases in a rear direction. In this case, the protruding part of the rear member 30 may be formed to have a V shape.

Meanwhile, although not shown, a rear member 30 according to a third embodiment of the present invention is formed at an angle b between first and second imaginary lines 31 and 32 at 180 degrees. That is, the rear member 30 is formed to extend so that a rear edge thereof is perpendicular to a central line of the flow path 111 in a longitudinal direction.

Figure 4:
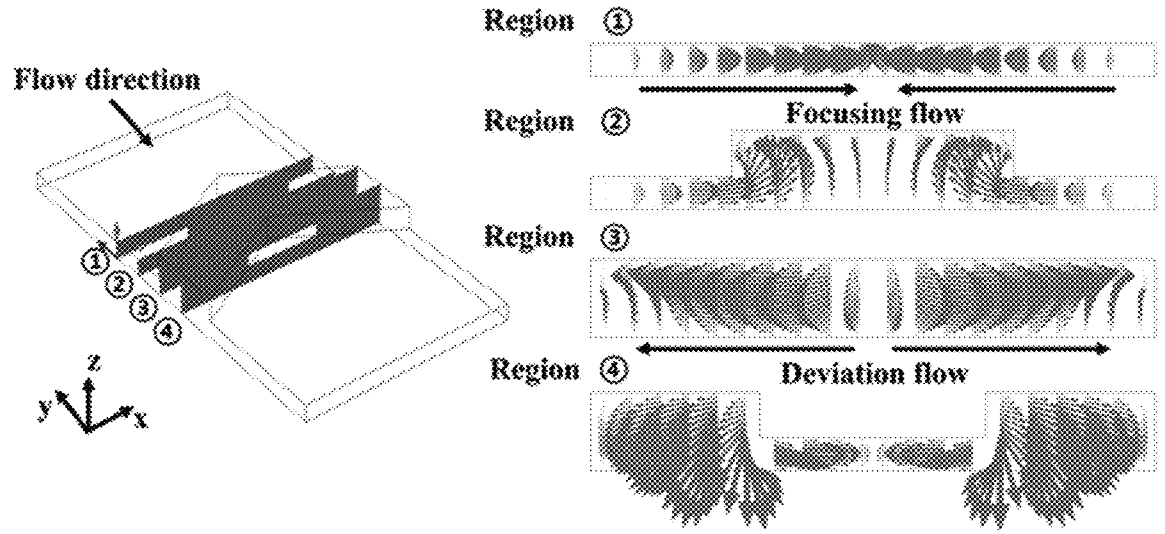
FIG. 4 shows simulation results showing a magnitude of a velocity vector of a fluid in a conventional herringbone-type fluid guiding unit through numerical analysis.
Figure 5:
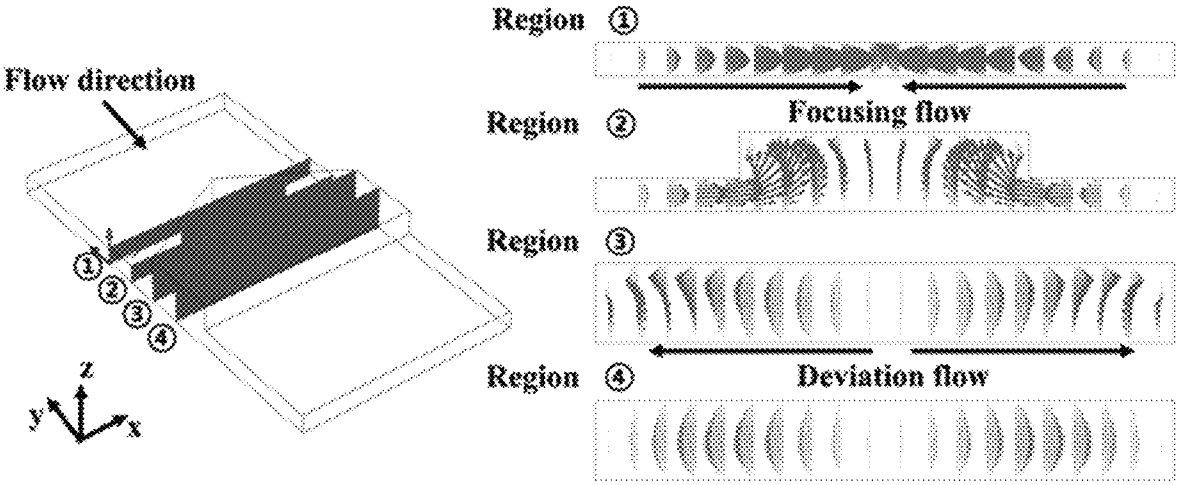
FIG. 5 shows simulation results showing a magnitude of a velocity vector of a fluid in the herringbone-type fluid guiding unit of the present invention through a numerical analysis.

FIGS. 4 and 5 show values of simulation results showing a magnitude of a velocity vector of a fluid in the conventional herringbone-type fluid guiding unit 10 and the herringbone-type fluid guiding unit 10 according to the third embodiment of the present invention through numerical analysis when a flow rate of the fluid is 100 ml/h. On left sides of FIGS. 4 and 5, positions at which velocity vectors of the conventional fluid guiding unit and the herringbone-type fluid guiding unit 10 according to the third embodiment of the present invention are calculated are shown, and first to fourth regions which are sequentially arranged from the front end part of the fluid guiding unit 10 in forward and rearward directions in the flow path 111 are shown. On right sides of FIGS. 4 and 5, velocity vectors of the fluid in the first to fourth ranges are shown.

Referring to FIGS. 4 and 5, focusing flows occur in the first regions, that is, the front end parts, of the conventional fluid guiding unit and the herringbone-type fluid guiding unit 10 according to the third embodiment of the present invention, and values of the focusing flows are similar. However, deviation flows occur in the third region and the fourth region, that is, the rear parts, of the conventional fluid guiding unit and the herringbone-type fluid guiding unit 10 according to the third embodiment of the present invention. A value of the deviation flow occurring in the herringbone-type fluid guiding unit 10 according to the third embodiment of the present invention is smaller than a value of the deviation flow occurring in the conventional fluid guiding unit. That is, it can be seen that, when an angle b between first and second imaginary lines 32 and 33 is greater than an angle a between third and fourth imaginary lines 21 and 22, the value of the deviation flow occurring in the rear part of the fluid induction unit 10 is smaller than the value of the deviation flow occurring in the conventional fluid guiding unit.

Figure 6:
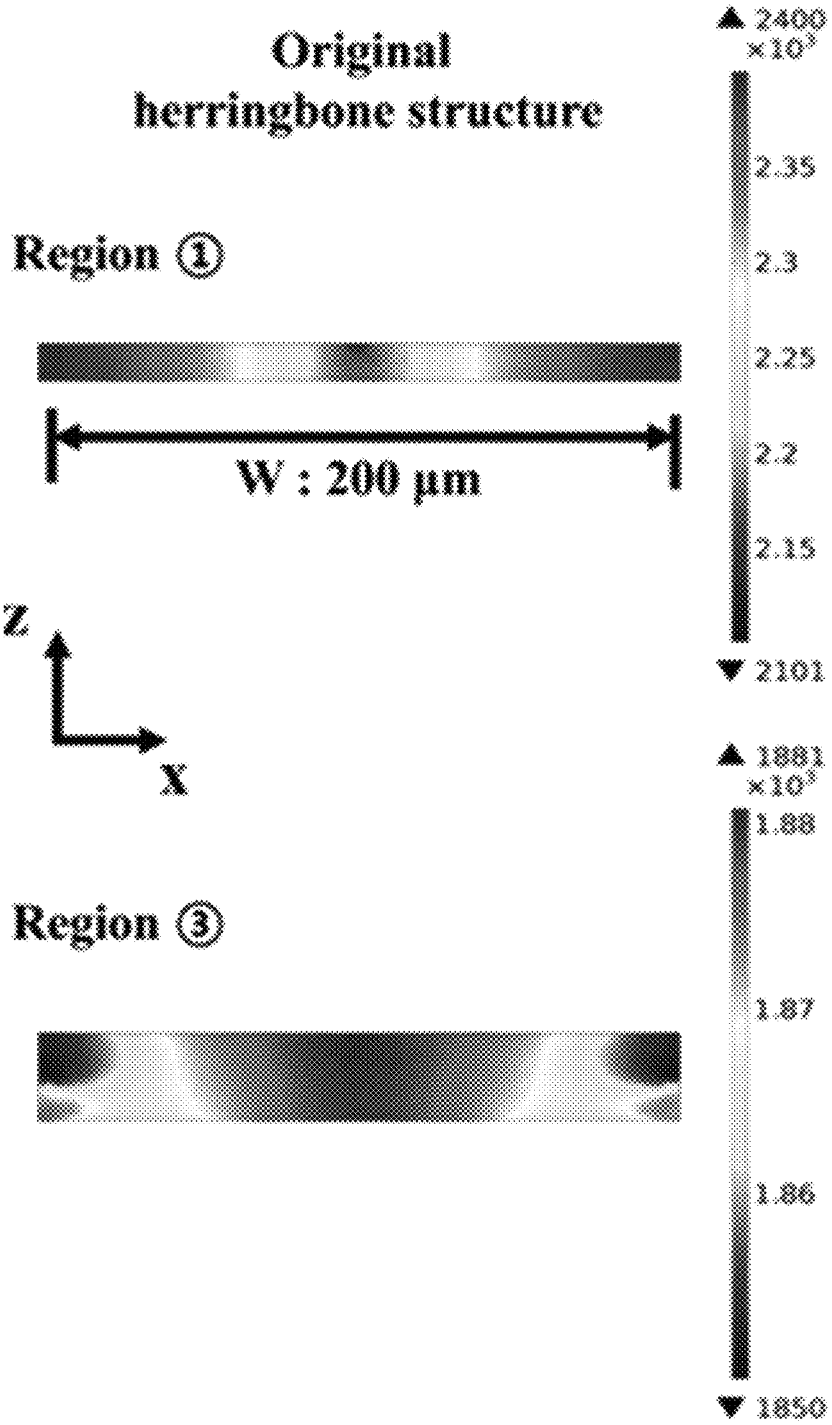
FIG. 6 shows pressure values in first and third regions of FIG. 4 in the conventional fluid guiding unit.
Figure 7:
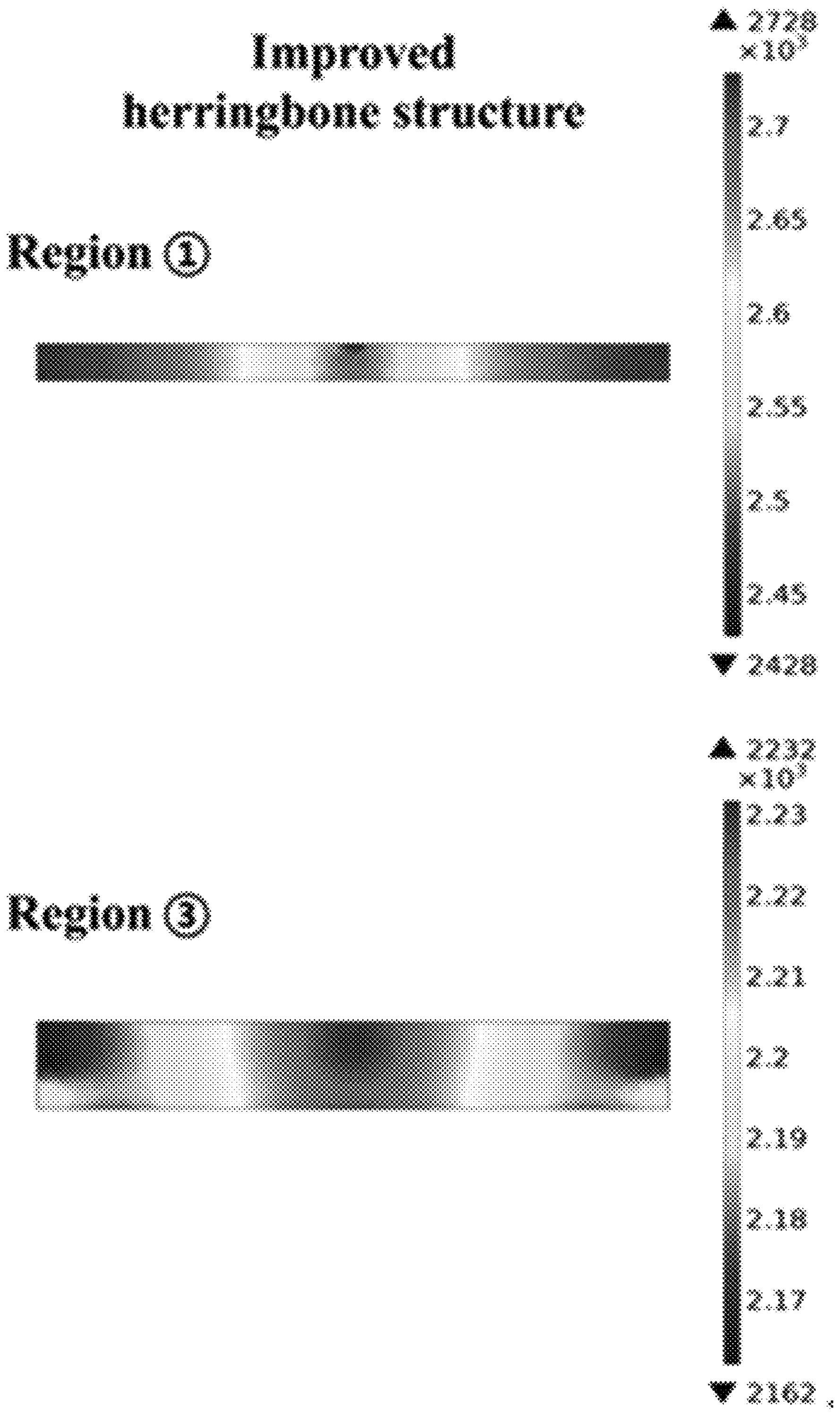
FIG. 7 shows pressure values in first and third regions of FIG. 5 in the herringbone-type fluid guiding unit of the present invention.
Figure 8:
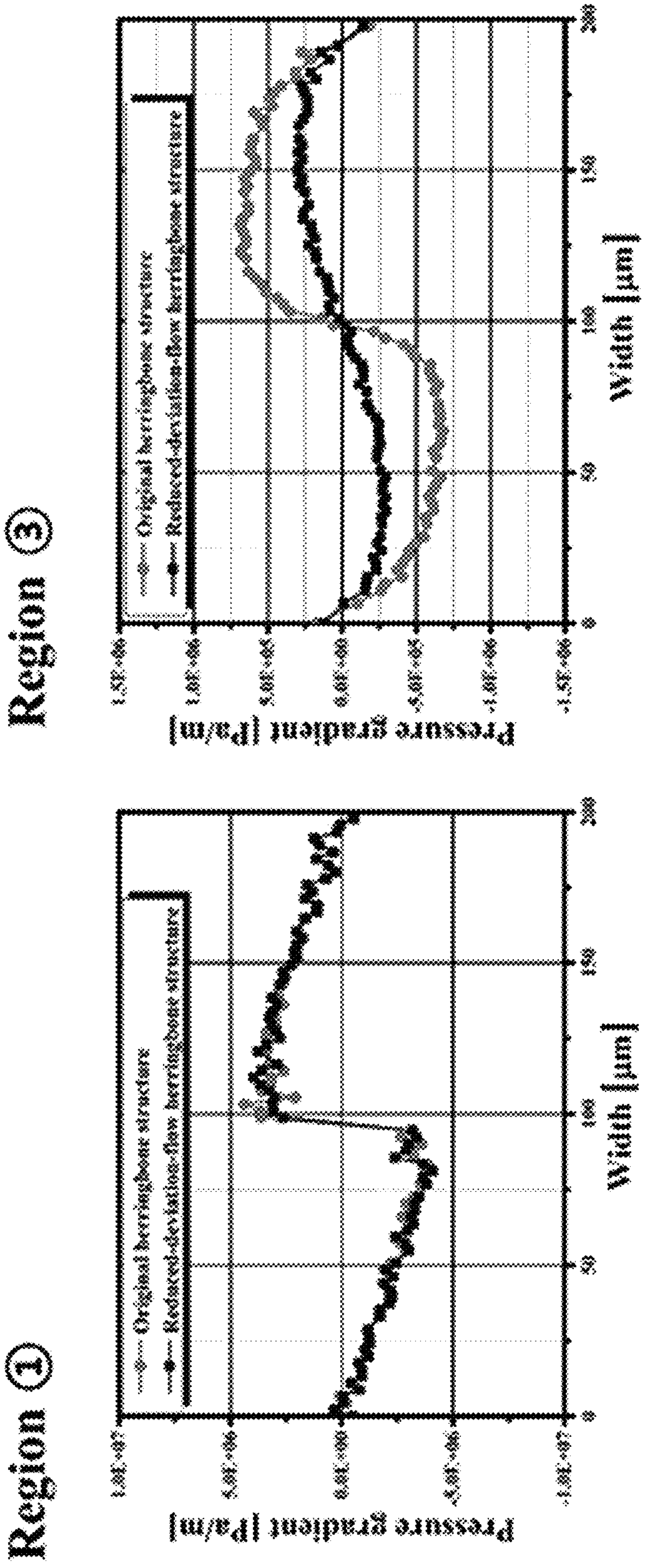
FIG. 8 shows pressure gradient values according to a width in the first and third regions of the conventional fluid guiding unit and the herringbone-type fluid guiding unit of the present invention.

Further, FIG. 6 shows pressure values in the first region and the third region of FIG. 4 in the conventional fluid guiding unit, FIG. 7 shows pressure values in the first region and the third region of FIG. 5 in the herringbone-type fluid guiding unit 10 according to the third embodiment of the present invention, and FIG. 8 shows pressure gradient values according to a width in the first region and the third region of the conventional fluid guiding unit and the herringbone-type fluid guiding unit 10 according to the third embodiment of the present invention. In this case, a red line of a graph in FIG. 8 shows pressure gradient values of the herringbone-type fluid guiding unit 10 according to the third embodiment of the present invention, and a black line of the graph in FIG. 8 shows pressure gradient values of the conventional fluid guiding unit.

Referring to FIGS. 6 to 8, it can be seen that the conventional fluid guiding unit and the herringbone-type fluid guiding unit 10 according to the third embodiment of the present invention all have the same pressure drop value of the focusing flow in the first region. However, in the third region, the pressure drop value of the deviation flow in the herringbone-type fluid guiding unit 10 according to the third embodiment of the present invention is smaller than the pressure drop value of the deviation flow in the conventional fluid guiding unit.

Figure 9:
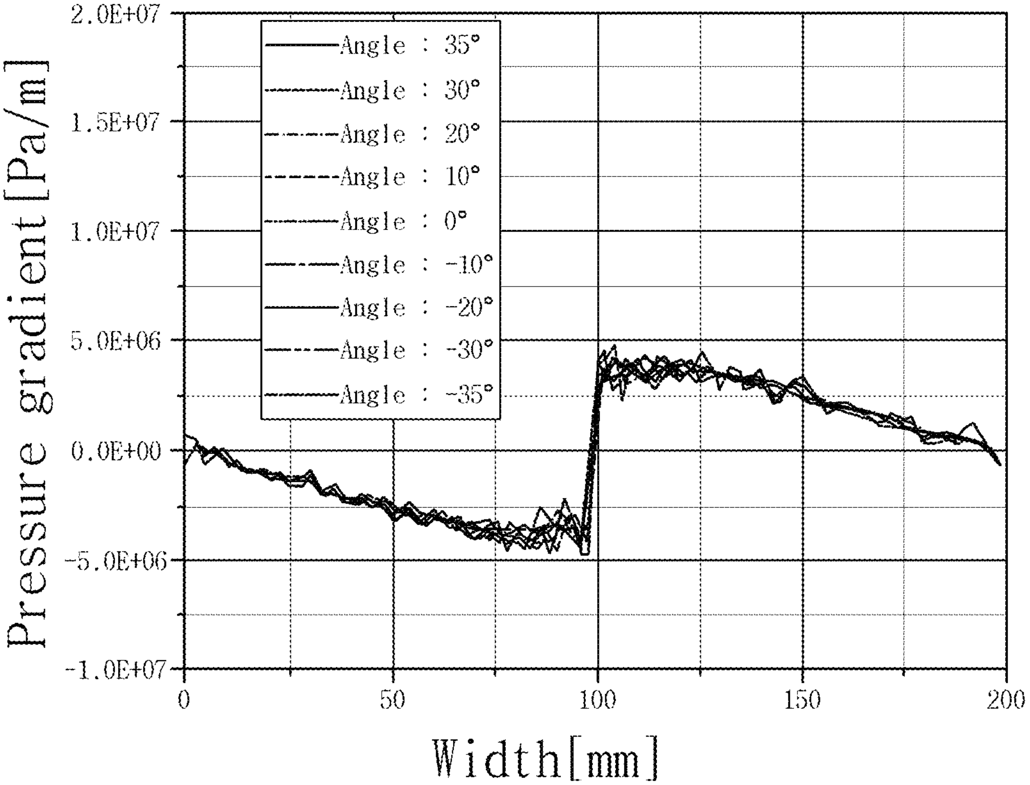
FIG. 9 shows pressure gradient values according to a lateral width in the first region of the herringbone-type fluid guiding unit of the present invention according to a change of an angle between first and second imaginary lines.
Figure 10:
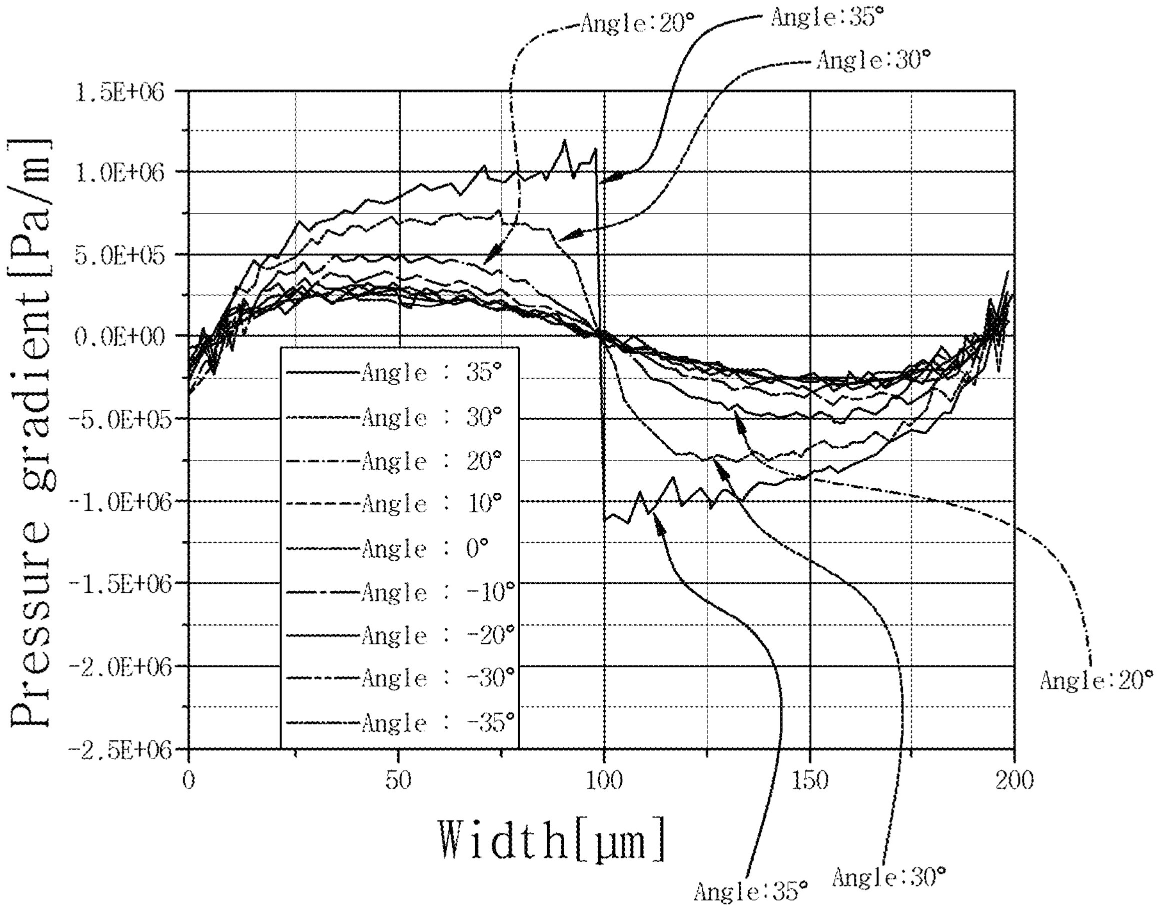
FIG. 10 shows pressure gradient values according to a lateral width in the third region of the herringbone-type fluid guiding unit of the present invention according to a change of an angle between the first and second imaginary lines.

Meanwhile, FIG. 9 shows pressure gradient values according to a lateral width in a first region according to a change of an angle b between first and second imaginary lines 32 and 33, and FIG. 10 shows pressure gradient values according to a lateral width in a third region according to a change of an angle b between first and second imaginary lines 32 and 33. Here, "Angle: 110" denotes the fluid guiding unit 10 in which the angle b between the first and second imaginary lines 32 and 33 is 110 degrees, "Angle: 120" denotes the conventional herringbone-type fluid guiding unit 10, which is the fluid guiding unit in which the angle b between the first and second imaginary lines 32 and 33 is 120 degrees, "Angle: 140" denotes a fluid guiding unit 10 in which the angle b between the first and second imaginary lines 32 and 33 is 140 degrees, "Angle: 160" denotes a fluid guiding unit 10 in which the angle b between the first and second imaginary lines 32 and 33 is 160 degrees, "Angle: 180" denotes the herringbone-type fluid guiding unit 10 according to the third embodiment of the present invention in which the angle b between the first and second imaginary lines 32 and 33 is 180 degrees, "Angle: –160" denotes the herringbone-type fluid guiding unit 10 according to the second embodiment of the present invention in which an angle b between the first and second imaginary lines 32 and 33 is 160 degrees, "Angle: –140" denotes the herringbone-type fluid guiding unit 10 according to the second embodiment of the present invention in which an angle b between the first and second imaginary lines 32 and 33 is 140 degrees, "Angle: –120" denotes the herringbone-type fluid guiding unit 10 according to the second embodiment of the present invention in which an angle b between the first and second imaginary lines 32 and 33 is 120 degrees, and "Angle: –110" denotes the herringbone-type fluid guiding unit 10 according to the second embodiment of the present invention in which an angle b between the first and second imaginary lines 32 and 33 is 110 degrees.

Referring to FIGS. 9 and 10, it can be seen that the conventional fluid guiding unit and the herringbone-type fluid guiding unit 10 according to the third embodiment of the present invention have similar pressure drop values of the focusing flow in the first region. However, the pressure drop values of the deviation flow decrease in the third region as the angle b between the first and second imaginary lines 32 and 33 increase. In this case, it can be seen that there is no large difference in pressure gradient value according to the width, between the herringbone-type fluid guiding unit 10 according to the first embodiment in which the angle b between the first and second imaginary lines 32 and 33 is 160 degrees or more and the herringbone-type fluid guiding unit 10 according to the second and third embodiments. Therefore, in the herringbone-type fluid guiding unit 10 according to the first embodiment, the angle b between the first and second imaginary lines 32 and 33 may be 160 degrees or more.

Figure 11:
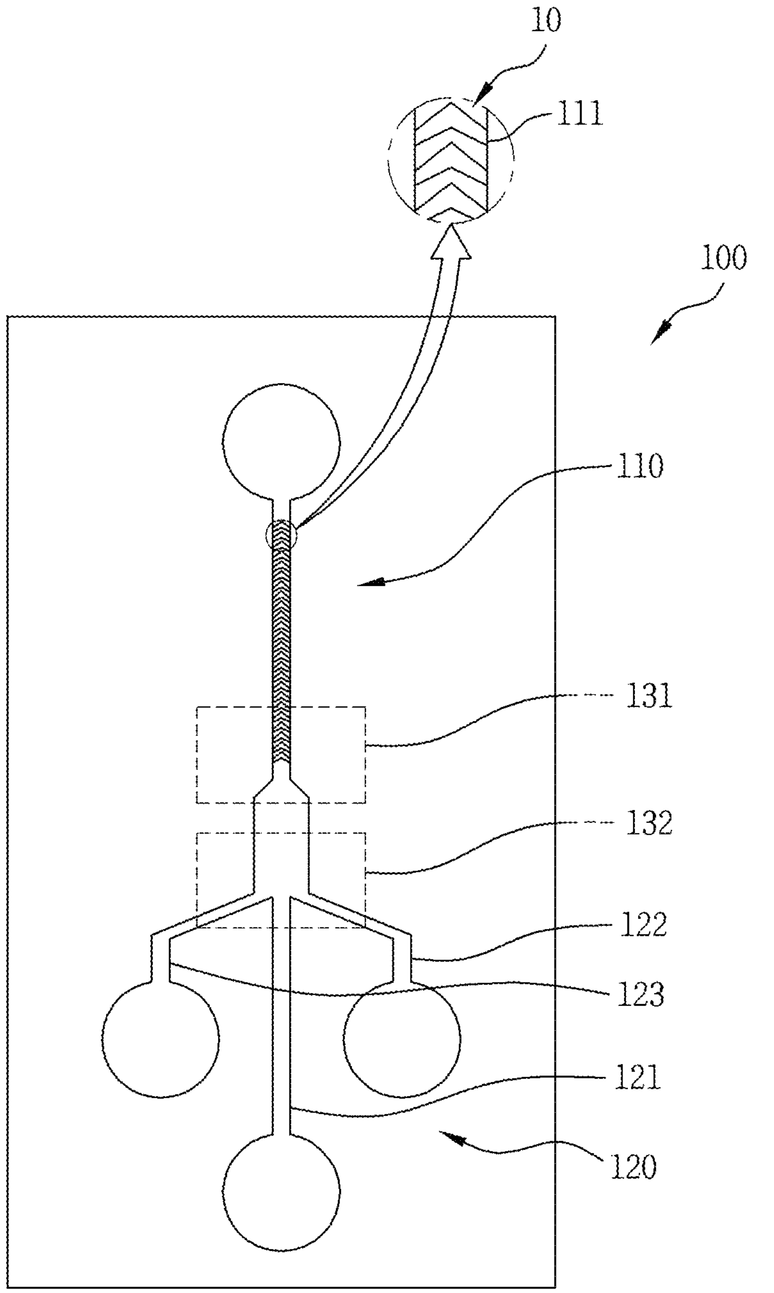
FIG. 11 is a cross-sectional view of a fluid concentration apparatus using the herringbone-type fluid guiding unit of the present invention.

Meanwhile, FIG. 11 shows a fluid concentration apparatus 100 using the herringbone-type fluid guiding unit 10 according to the present invention.

Referring to the drawing, the fluid concentration apparatus 100 includes a main body 110 provided with a flow path 111 through which a fluid containing cells or fine particles to be separated therein flows, a plurality of herringbone-type fluid guiding units which are provided on the flow path 111 so as to interfere with a flow of the fluid to guide the cells or fine particles to be separated toward an inner side surface of the flow path 111 and are arranged to be spaced apart from each other in forward and rearward directions with respect to a flow direction of the fluid, and a discharge part 120 which is provided in the main body 110 at a position spaced apart rearward from the herringbone-type fluid guiding units and collects and discharges the cells or fine particles to be separated which are guided into the inner side surface of the flow path 111.

The flow path 111 extending in forward and rearward directions is provided inside the main body 110, and a fluid supply unit (not shown) for supplying a fluid is connected to a front end part of the flow path 111. The fluid containing the cells or fine particles to be separated which are supplied from the fluid supply unit flows to the discharge part 120 along the flow path 111.

Since the herringbone-type fluid guiding unit is one of the above-described herringbone-type fluid guiding units according to the first to third embodiments of the present invention, a detailed description thereof will be omitted. Since the focusing flow occurs in the front part of each of the herringbone-type fluid guiding units and the deviation flow occurs in the rear part, the cells or fine particles contained in the fluid pass through the plurality of herringbone-type fluid guiding units so that the fluid passing through the flow path 111 is guided to left and right inner side surfaces of a flow lock.

The discharge part 120 includes a first discharge path 121 and a plurality of second discharge paths 122 and 123, which are in communication with the flow path 111 of the main body 110. In this case, the second discharge paths 122 and 123 may be disposed on left and right sides of the discharge part 120 with respect to the first discharge path 121 so that the cells or fine particles to be separated which are guided into the inner side surface of the flow path 111 are introduced to the second discharge paths 122 and 123.

Although not shown, a first collecting container for accommodating a fluid from which cells or fine particles are separated is connected to a rear end part of the first discharge path 121, and a second collecting container for accommodating a fluid having a high concentration of the cells or fine particles is connected to a rear end part of each of the second discharge paths 122 and 123.

Figure 12:
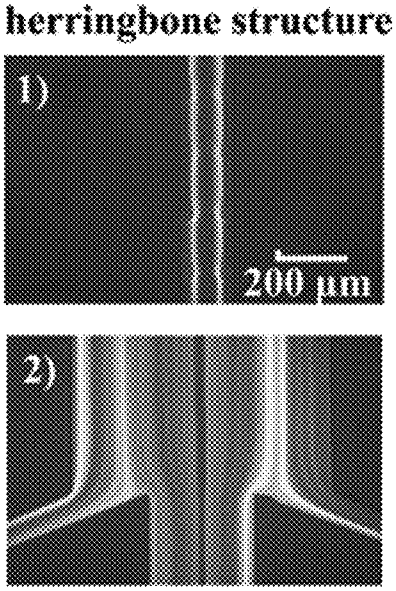
FIG. 12 shows microscope images showing a fluid flow of a fluid concentration apparatus to which a conventional herringbone-type fluid guiding unit is applied when viewed at a first position and a second position of FIG. 11.
Figure 13:
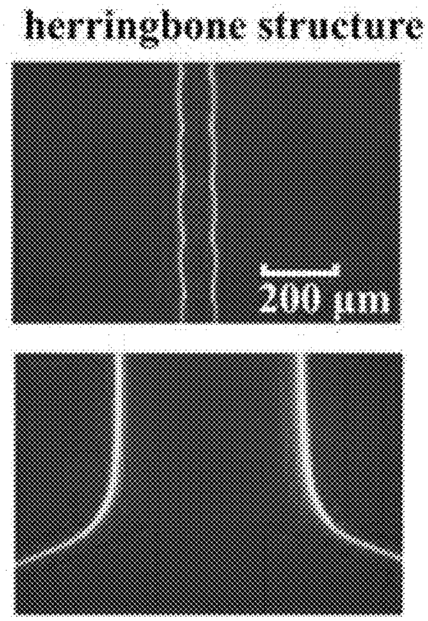
FIG. 13 shows microscope images showing a fluid flow of a fluid concentration apparatus to which the herringbone-type unit of the present invention is applied when viewed at the first position and the second position of FIG. 11.

Meanwhile, FIGS. 12 and 13 show microscope images showing the fluid flow of the fluid concentration apparatus 100 to which the conventional herringbone-type fluid guiding unit 10 is applied and the fluid flow of the fluid concentration apparatus 100 to which the herringbone-type fluid guiding unit according to the third embodiment of the present invention is applied when viewed at a first position and a second position of FIG. 11. Here, the fluid flowing inside the flow path 111 contains 4.8 μm of particles therein and flows at a flow rate of 100 ml/h.

Referring to the drawings, it can be seen that, since the value of the deviation flow occurring in the rear part of the conventional fluid guiding unit 10 having the herringbone structure is greater than the value of the deviation flow occurring in the herringbone-type unit according to the third embodiment of the present invention, a relatively large amount of fine particles are introduced into the first discharge path 121.

Figure 14:
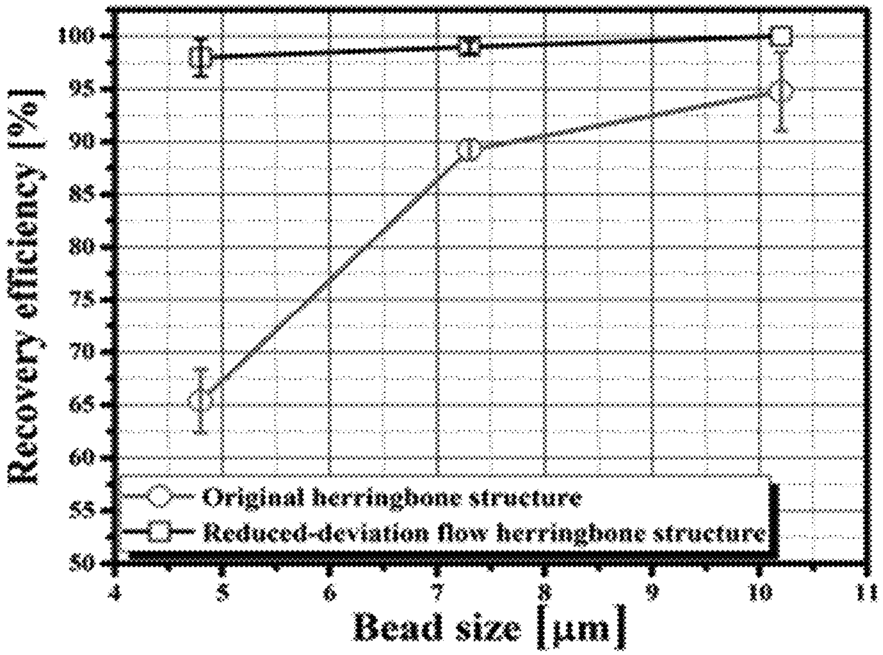
FIG. 14 is a graph showing recovery efficiency of the fluid concentration apparatus to which the conventional herring-bone-type fluid guiding unit is applied and recovery efficiency of the fluid concentration apparatus to which the herringbone-type unit of the present invention is applied according to a bead size of fine particles.

Further, FIG. 14 is a graph showing recovery efficiency of the fluid concentration apparatus 100 to which the conventional herringbone-type fluid guiding unit is applied and recovery efficiency of the fluid concentration apparatus 100 to which the herringbone-type unit according to the third embodiment of the present invention is applied according to a bead size of fine particles. Here, a red line of the graph indicates the recovery efficiency of the fluid concentration apparatus 100 to which the conventional herringbone-type fluid guiding unit 10 is applied, and a black line of the graph indicates the recovery efficiency of the fluid concentration apparatus 100 to which the herringbone-type unit according to the third embodiment of the present invention is applied. Further, the recovery efficiency is a value obtained by dividing the number of fine particles introduced into the second discharge paths 122 and 123 by the number of fine particles introduced into the first and second discharge paths 121, 122, and 123.

Referring to the drawing, it can be seen that the recovery efficiency of the fluid concentration apparatus 100 to which the herringbone-type unit according to the third embodiment of the present invention is applied is higher than the recovery efficiency of the fluid concentration apparatus 100 to which the conventional herringbone-type fluid guiding unit 10 is applied. In particular, it can be seen that the fluid concentration apparatus 100 to which the herringbone-type unit according to the third embodiment of the present invention is applied exhibits similar recovery efficiency according to the size of the fine particles. However, the recovery efficiency of the fluid concentration apparatus 100 to which the conventional herringbone-type fluid guiding unit 10 is applied decreases as the size of the fine particles decreases.

In the herringbone-type fluid guiding unit 10 and the fluid concentration apparatus 100 using the same according to the present invention as described above, the fluid guiding unit 10 for interfering with a fluid is formed to have an angle at a front end part greater than an angle at a rear end part, and thus it is possible to reduce a value of a pressure drop of the fluid flow occurring in the rear part of the fluid guiding unit 10 so that recovery efficiency of the cells with respect to the fluid may be improved.

The description of the disclosed embodiments is provided to enable those skilled in the art to use or embody the present invention. Various modifications of the embodiments will become clear to those skilled in the art, and the generic principles defined herein may be applied to other embodiments without departing from the scope of the invention. Therefore, the present invention is not intended to be limited to the embodiments described herein but should be construed as broadly consistent with the principles and new features set forth herein.

INDUSTRIAL APPLICABILITY

The present invention can be applied to techniques for extracting proteins or nucleic acids from biological samples such as cells, bacteria, or viruses in order to diagnose, treat, or prevent diseases at a genetic level, and to techniques for extracting proteins or nucleic acids from biological samples in various fields such as customized new drug development, forensic medicine, and environmental hormone detection in addition to the diagnosis, treatment, or prevention of diseases.

The invention claimed is:

1. A fluid concentration apparatus, comprising:

a main body having a flow path through which a fluid flows, wherein the flow path guides cells or fine particles contained in the fluid from a first point to a second point; and a discharge part, wherein the main body comprises:

a plurality of fluid guiding units, wherein each fluid guiding unit of the plurality of fluid guiding units is provided on the flow path and comprises:

a top surface, a left side surface, a right side surface, a left-front surface, a right-front surface, a left-rear surface, a right-rear surface, and a bottom surface, wherein:

each of the left side surface, the right side surface, the left-front surface, the right-front surface, the left-rear surface, and the right-rear surface is directly connected with the top surface and the bottom surface;

the left side surface is directly connected with the left-front surface and the left-rear surface;

the right side surface is directly connected with the right-front surface and the right-rear surface;

the left-front surface is directly connected with the left side surface and the right-front surface;

the right-front surface is directly connected with the right side surface and the left-front surface;

the left-rear surface is directly connected with the left side surface and the right-rear surface;

the right-rear surface is directly connected with the right side surface and the left-rear surface;

the left side surface has a first edge that is shared by the left side surface and the top surface, and a second edge that is shared by the left side surface and the left-rear surface;

a length of the first edge is longer than a length of the second edge;

the right side surface has a third edge that is shared by the right side surface and the top surface, and a fourth edge that is shared by the right side surface and the right-rear surface;

a length of the third edge is longer than a length of the fourth edge;

the first edge is positioned parallel to the third edge;

a first angle at the direct connection between the left-rear surface and the right-rear surface is greater than a second angle at the direct connection between the left-front surface and the right-front surface; and the first angle is 180°, wherein:

a front part of the fluid guiding unit has a lateral width, that increases in a rear direction from a front end part of the front part; and a rear part of the fluid guiding unit is extending rearward from the front part, wherein the discharge part comprises a first discharge path, a second discharge path, a third discharge path, a first round-shaped collecting container, a second round-shaped collecting container, and a third round-shaped collecting container, wherein the first discharge path, the second discharge path, and the third discharge path are in communication with the flow path of the main body, wherein the second discharge path and the third discharge path have the same length, and a length of the first discharge path is longer than the length of the second discharge path and the third discharge path, wherein the first discharge path has a shape of a first straight line, and each of the second discharge path and the third discharge path has a shape that is consisted of: an inclined straight line, which extends in a direction to away from the first discharge path; a second straight line; and a connecting part, which connects the inclined straight line and the second straight line with an angle, wherein the second discharge path is disposed on a left side of the discharge part with respect to the first discharge path, and the third discharge path is disposed on a right side of the discharge part with respect to the first discharge path, so that the cells or fine particles to be separated which are guided into the inner side surface of the flow path are introduced to the second discharge path and the third discharge path, wherein a distal end of the first discharge path is connected to the first round-shaped collecting container, a distal end of the second discharge path is connected to the second round-shaped collecting container, and a distal end of the third discharge path is connected to the third round-shaped collecting container, and wherein the first round-shaped collecting container, the second round-shaped collecting container, and the third round-shaped collecting container are separated from each other.

2. The fluid concentration apparatus of claim 1, wherein the front part is formed to have an inverted-V shape.

* * * * *